United States Patent [19]

Umezawa et al.

[11]  4,268,664

[45]  May 19, 1981

[54] PROCESS FOR THE PREPARATION OF 1-N-ISOSERYL- OR 1-N-(L-4-AMINO-2-HYDROXYBUTYRYL)-3',4'-DIDEOXYKANAMYCIN B AND INTERMEDIATES THEREOF

[75] Inventors: Hamao Umezawa, Tokyo; Shinichi Kondo, Yokohama, both of Japan

[73] Assignee: Zaidan Hojin Biseibutsu Kagaku Kenkyu Kai, Japan

[21] Appl. No.: 97,896

[22] Filed: Nov. 26, 1979

[30] Foreign Application Priority Data

Dec. 14, 1978 [JP]  Japan ................................ 53-153651

[51] Int. Cl.$^3$ ...................... C07H 15/22; A61K 31/71
[52] U.S. Cl. ...................................... 536/10; 424/180; 536/17 R
[58] Field of Search ................................ 536/10, 17 R

[56] References Cited

U.S. PATENT DOCUMENTS

| | | | |
|---|---|---|---|
| Re. 28,647 | 12/1975 | Umezawa et al. | 536/10 |
| 3,781,268 | 12/1973 | Kawaguchi et al. | 536/10 |
| 3,939,143 | 2/1976 | Umezawa et al. | 536/10 |
| 4,107,424 | 8/1978 | Umezawa et al. | 536/10 |
| 4,156,078 | 5/1979 | Umezawa et al. | 536/10 |
| 4,169,939 | 10/1979 | Umezawa et al. | 536/10 |

*Primary Examiner*—Johnnie R. Brown
*Attorney, Agent, or Firm*—Larson, Taylor and Hinds

[57] ABSTRACT

1-N-Isoseryl- or 1-N-(L-4-amino-2-hydroxybutyryl)-3',4'-dideoxykanamycin B is prepared through a new route starting from 3',4'-dideoxy-3',4'-didehydrokanamycin B, which comprises the steps of protecting all or some of the four amino groups other than the 1-amino group of the starting material with an amino-protecting group, reacting the partially amino-protected derivative or derivatives thus formed with isoserine or L-4-amino-2-hydroxybutyric acid or a reactive derivative thereof having the amino group unprotected or protected whereby to acylate the 1-amino group of the former, eliminating the amino-protecting group or groups from the acylated product and reducing the 3',4'-olefinic double bond of the product by catalytic hydrogenation, the last two steps being effected in order or simultaneously or in the reverse order. Also provided are new, useful intermediate compounds during the process.

12 Claims, No Drawings

PROCESS FOR THE PREPARATION OF 1-N-ISOSERYL- OR 1-N-(L-4-AMINO-2-HYDROXYBUTYRYL)-3',4'-DIDEOXYKANAMYCIN B AND INTERMEDIATES THEREOF

SUMMARY OF THE INVENTION

This invention relates to a new process for the preparation of 1-N-isoseryl- or 1-N-(L-4-amino-2-hydroxybutyryl)-3',4'-dideoxykanamycin B in a high yield from 3',4'-dideoxy-3',4'-didehydrokanamycin B as a starting material and to new, useful intermediates thereof.

BACKGROUND OF THE INVENTION

3',4'-Dideoxykanamycin B which was synthetically derived by us from kanamycin B (refer to Japanese Patent Publications Nos. 7595/75 and 46110/76; U.S. Pat. No. 3,753,973) has been used widely as a chemotherapeutic agent characterized by its high activity against kanamycin-resistant microbial strains including *Pseudomonas aeruginosa*. More recently, 1-N-(L-4-amino-2-hydroxybutyryl)-3',4'-dideoxykanamycin B (refer to Japanese Patent Publication No. 33629/77; U.S. Pat. No. 4,107,424) and 1-N-isoseryl-3',4'-dideoxykanamycin B (refer to Japanese Patent Prepublication No. 47949/75; U.S. Pat. No. 3,939,143) were synthesized also by us and found to exhibit a high activity against a wide variety of drug-resistant microbial strains including *Pseudomonas aeruginosa*. Our continued studies of these kanamycin derivatives have now resulted in the development of a new, convenient route for large-scale preparation of 1-N-isoseryl- or 1-N-(L-4-amino-2-hydroxybutyryl)-3',4'-dideoxykanamycin B.

BRIEF SUMMARY OF THE INVENTION

According to this invention, therefore, there is provided a process for the preparation of 1-N-isoseryl-3',4'-dideoxykanamycin B or 1-N-(L-4-amino-2-hydroxybutyryl)-3',4'-dideoxykanamycin B of the formula:

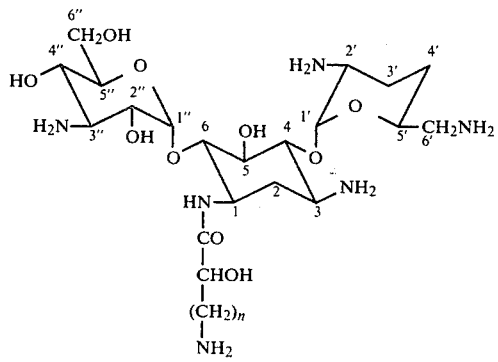

where n is 1 or 2 which comprises (1) providing 3',4'-dideoxy-3',4'-didehydrokanamycin B of the formula:

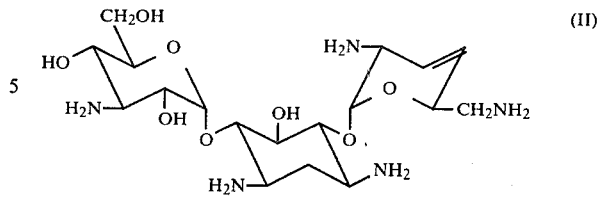

i.e. 3',4'-dideoxy-3'-enokanamycin B so-called (refer to Japanese Patent Prepublication No. 71445/77; U.K. Pat. No. 1,537,905) as starting compound, (2) protecting all or some of the four amino groups other than the 1-amino group of the compound with an amino-protecting group, (3) reacting the partially amino-protected derivative or derivatives thus obtained with isoserine or L-4-amino-2-hydroxybutyric acid or a reactive derivative thereof having the amino group unprotected or protected with an amino-protecting group to acylate the 1-amino group of the former, (4) eliminating the amino-protecting group or groups of the acylated product and (5) reducing the 3',4'-olefinic double bond of the product by a catalytic hydrogenation, the steps (4) and (5) being effected in order or simultaneously or in the reverse order as known.

In comparison with such a known process that 3',4'-dideoxykanamycin B is synthetically derived from kanamycin B according to the methods of Japanese Patent Publications Nos. 7595/75 and 46110/76 (see U.S. Pat. No. 3,753,973) and the resulting 3',4'-dideoxykanamycin B is reacted with L-4-amino-2-hydroxybutyric acid or isoserine by condensation at the 1-amino group to give the object compound of formula I according to the method of Japanese Patent Publication No. 33629/77 (see U.S. Pat. No. 4,107,424) or Japanese Patent Prepublication No. 47949/75 (see U.S. Pat. No. 3,939,143), the process according to this invention is advantageous from the industrial point of view in that it can reduce the number of reaction steps required and gives an improved overall yield from the starting kanamycin B.

DETAILED DESCRIPTION OF THE INVENTION

The process of this invention is explained here in detail. The amino-protecting group to be used to partially protect the amino groups of the starting 3',4'-dideoxy-3',4'-didehydrokanamycin B of formula II may be any of known, conventional amino-protecting groups. Typical examples of amino-protecting groups include alkyloxycarbonyl such as tert-butoxycarbonyl and tert-amyloxycarbonyl; cycloalkyloxycarbonyl such as cyclohexyloxycarbonyl; aralkyloxycarbonyl such as benzyloxycarbonyl; acyl such as trifluoroacetyl and o-nitrophenoxyacetyl; phosphinothioyl such as diphenylphosphinothioyl and dimethylphosphinothioyl; and phosphinyl such as diphenylphosphinyl. Bivalent amino-protecting groups such as phthaloyl may also be used. Protection of amino groups in the form of a Schiff base is also utilizable. The step (2) for the introduction of these amino-protecting groups into the compound of formula II may be carried out by any of processes known per se in the syntheses of peptides and other organic compounds, for example those using an acid halide, acid azide, active ester or acid anhydride as an amino-protecting group-introducing reagent, as described, for example, in U.S. Pat. No. 4,107,424. Depending upon the amount of amino-protecting group-introducing reagent used which is in the range of 0.5 to 6 molar equivalents, it is possible to produce a series of different, partially amino-protected derivatives of 3',4'-dideoxy-3',4'-didehydrokanamycin B in any desired proportion due to the difference in reactivity among the respective amino groups on the starting compound.

In the process of this invention, the partially amino-protected derivative of 3',4'-dideoxy-3',4'-didehydrokanamycin B may be any possible such derivative wherein all or some, i.e. at least one, of the four amino groups other than the 1-amino group of 3',4'dideoxy-3',4'-didehydrokanamycin B is protected with an amino-protecting group. For example, 3,2',6',3"-tetra-N-protected derivative of formula III, 3,2',6'- and 2',6',3"-tri-N-protected derivatives of formula IV and V, respectively, 2',6'-di-N-protected derivative of formula VI and 6'-mono-N-protected derivative of formula VII may be used, among which the first three compounds are most preferred.

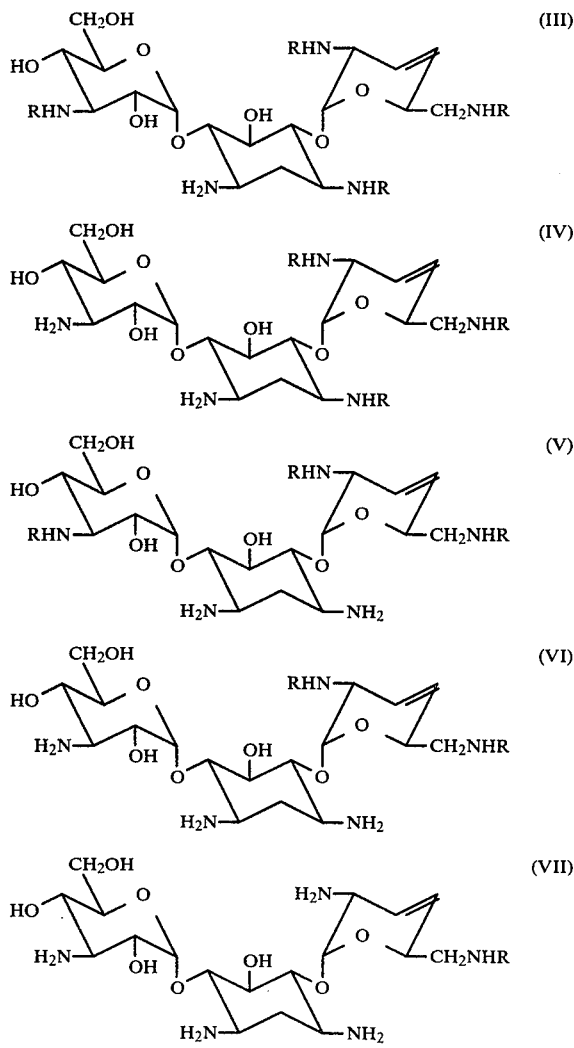

Mixtures of such partially amino-protected derivatives of 3',4'-dideoxy-3',4'-didehydrokanamycin B may also be used in the subsequent acylation step, i.e. the step (3). It is therefore convenient for the acylation step to use a crude product of the amino-protecting step which is usually a mixture of partially amino-protected derivatives of 3',4'-dideoxy-3',4'-didehydrokanamycin B as it is without purifying it. Thus, in a preferred embodiment of the amino-protecting step according to the process of this invention, the amino-protecting group-introducing reagent may be used in an amount of 3 to 5 molar equivalents in an aqueous organic solvent. One typical example of the amino-protecting step is given below.

3',4'-Dideoxy-3',4'-didehydrokanamycin B (4 mmol) is dissolved in a 50% aqueous isopropyl alcohol (90 ml) and trimethylamine (2.2 ml). To the resulting solution, tertbutyl-S-4,6-dimethylpyrid-2-ylthiocarbonate (16 mmol) is added as tert-butoxycarbonyl group-introducing reagent and the mixture is stirred at 50° C. for 23 hours and then concentrated to dryness in vacuo. The residue is subjected to a silica gel-column chromatography to isolate the 3,2',6',3"-tetra-N-tert-butoxycarbonyl derivative (0.22 mmol, 5.5%), the 2',6',3"-tri-N-tert-butoxycarbonyl derivative (0.26 mmol, 6.5%), the 3,2',6'-tri-N-tert-butoxycarbonyl derivative (0.83 mmol, 20.8%), the 2',6'-di-N-tert-butoxycarbonyl derivative (1.02 mmol, 25.5%) and the 6'-N-tert-butoxycarbonyl derivative (0.33 mmol, 8.3%).

An alternative method for the introduction of an amino-protecting group, which may be useful for the amino-protecting step of the process according to this invention, is described in our copending Japanese Patent Application No. 138402/78 filed on Nov. 11, 1978 and our copending U.S. Patent Application Ser. No. 090,591, filed on Nov. 2, 1979 relating to a "zinc-complex" process for the preparation of aminoglycosidic antibiotics having some of the amino groups selectively protected. According to this alternative method, the starting compound of formula II is first converted into a complex thereof with zinc cation and then acylated into a partially amino-protected derivative.

In the subsequent acylation step of the process according to this invention, the 1-amino group of a partially amino-protected derivative or derivatives of 3',4'-dideoxy-3',4'-didehydrokanamycin B formed in the preceding amino-protecting step is acylated with DL-, D- or L-isoserine or L-4-amino-2-hydroxybutyric acid with the amino group being unprotected or protected with an amino-protecting group. The acylation may be effected by any of known methods for the syntheses of amides including dicyclohexylcarbodiimide process, mixed acid anhydrides process, acid azide process and active ester process (see, for example, U.S. Pat. Nos. 3,781,268, 4,001,208 and 4,107,424), where DL-, D- or L-isoserine [3-amino-2-hydroxypropionic acid] or L-4-amino-2-hydroxybutyric acid or a reactive derivative (a functional equivalent) thereof is used as acylating agent. The amino-protecting group used for the protection of the amino group of isoserines or L-4-amino-2-hydroxybutyric acid may be the same as, or different from, those used for the protection of one or more amino groups other than the 1-amino group of 3',4'-dideoxy-3',4'-didehydrokanamycin B in the amino-protecting step above-mentioned. Tertiary-butoxycarbonyl group is an example of preferred amino-protecting groups in that it can be easily eliminated or removed by a treatment with an acid solution such as an aqueous solution of trifluoroacetic acid, acetic acid and the like or dilute hydrochloric acid. Another example of preferred amino-protecting groups is benzyloxycarbonyl group because it can be eliminated by a conventional catalytic reduction using a platinum group metal catalyst, when the reduction of 3',4'-olefinic unsaturation can be effected simultaneously.

Preferably, the acylation is carried out by using an active ester in an aqueous solvent. Thus, there may be used, as an active ester obtainable in a usual way, N-hydroxysuccinimide ester of isoserine or of L-4-benzyloxycarbonylamino-2-hydroxybutyric acid, for example, in an amount of 0.5 to 2 molar equivalents, preferably 1 to 1.5 molar equivalents. As a water-miscible solvent, there may be used preferably dioxane, 1,2-dimethoxyethane, N,N-dimethylformamide, tetrahydrofuran, triethylamine and the like.

In the acylation step, the 1-amino group of a partially amino-protected derivative or derivatives of 3',4'-dideoxy-3',4'-didehydrokanamycin B is acylated with isoserine or L-4-amino-2-hydroxybutyric acid or a reactive derivative thereof to give the product of the formula:

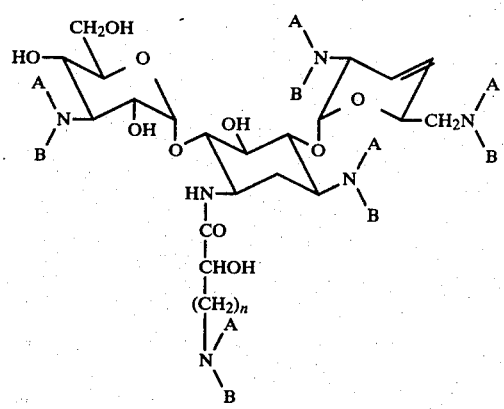

wherein each pair of A and B represent a pair of hydrogen and a monovalent amino-protecting group or each pair of A and B taken together form a bivalent amino-protecting group, provided that in any one to four pairs of A and B among the total five pairs both A and B may represent hydrogen atoms; and n is 1 or 2.

The step (4) for the elimination or removal of the amino-protecting group or groups from the acylation product may be carried out in a usual manner. Thus, the amino-protecting groups of alkyloxycarbonyl type may be eliminated by the hydrolysis with an acid solution such as an aqueous solution of trifluoroacetic acid, acetic acid and the like or dilute hydrochloric acid. In case of aralkyloxycarbonyl groups such as benzyloxycarbonyl, the elimination thereof may be easily effected by a usual catalytic reduction, i.e. hydrogenolysis. The utilization of such a catalytic reduction for the elimination of amino-protecting group or groups of aralkyloxycarbonyl type is advantageous for the purpose of this invention in that the catalytic reduction simultaneously attacks on the site of the 3',4'-olefinic double bond of the acylated product to hydrogenate it, thus yielding the desired 1-N-isoseryl- or 1-N-(L-4-amino-2-hydroxybutyryl)-3',4'-dideoxykanamycin B in one step.

In usual, in the process of this invention, the elimination of the amino-protecting group or groups from the acylated product of formula (VIII) is followed by the saturation of the 3',4'-double bond by hydrogenation as above-mentioned. In case of hydrogenolysis being applied to eliminate the amino-protecting group or groups, the hydrogenation of the 3',4'-double bond can occur concurrently therewith, so that no further step will be required for the saturation of the 3',4'-double bond.

It will be apparent to the skilled in the art that the sequence of the step (4) of eliminating the amino-protecting group(s) and the step (5) of hydrogenating the 3',4'-double bond can be reversed so that the hydrogenation step is followed by the elimination step.

The hydrogenation of the 3',4'-olefinic double bond may be carried out by reduction with hydrogen in the presence of a known hydrogenation catalyst, for example a platinum group metal catalyst such as platinum, platinum oxide and palladium. The reduction may be effected at room temperatures or under heating.

According to another aspect of this invention, we provide new compounds of the formula:

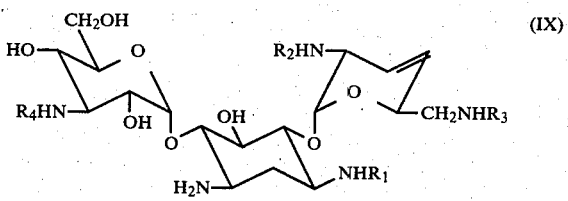

wherein $R_1$, $R_2$, $R_3$ and $R_4$ are the same or different and each represent hydrogen atom or tert-butoxycarbonyl group, provided at least one of them represents tert-butoxycarbonyl group, that is amino-protected derivatives of 3',4'-dideoxy-3',4'-didehydrokanamycin B synthesized as useful intermediate compounds by the process of this invention. Typical properties of such new compounds are given below.

(i) 3,2',6',3''-Tetra-N-tert-butoxycarbonyl-3',4'-dideoxy-3',4'-didehydrokanamycin B of formula IX wherein $R_1$, $R_2$, $R_3$ and $R_4$ each represent tert-butoxycarbonyl group is in the form of a white powder, decomposes at 143°–150° C. and has a specific rotation $[\alpha]_D^{26} = +17°$ (c=1, methanol) and its elemental analysis coincides with the theoretical values of $C_{38}H_{67}N_5O_{16}\cdot 2H_2O$ (C 51.51%, H 8.08%, N 7.90%). This substance gives a single spot positive to ninhydrin reaction at Rf 0.91 on a thin layer chromatography of silica gel (available under a trade name "Art. 5721", a product of Merck Co., West Germany) with a solvent system of butanolethanol-chloroform-17% aqueous ammonia (4:5:2:2 by volume) as developer.

(ii) 3,2',6'-Tri-N-tert-butoxycarbonyl-3',4'-dideoxy-3',4'-didehydrokanamycin B of formula IX wherein $R_4$ is hydrogen and $R_1$, $R_2$ and $R_3$ each represent tert-butoxycarbonyl group is in the form of a white powder with a decomposition point of 154°–158° C., a specific rotation $[\alpha]_D^{26} = +14°$ (c=1, methanol) and values of elemental analysis coincident with the theoretical values of $C_{33}H_{59}N_5O_{14}\cdot H_2O$ (C 51.62%, H 8.01%, N 9.12%). This substance gives a single spot positive to ninhydrin reaction at Rf 0.48 on the same thin layer chromatography as in (i) above.

(iii) 2',6',3''-Tri-N-tert-butoxycarbonyl-3',4'-dideoxy-3',4'-didehydrokanamycin B of formula IX wherein $R_1$ is hydrogen and $R_2$, $R_3$ and $R_4$ each represent tert-butoxycarbonyl group is in the form of a white powder with a decomposition point of 130°–133° C., a specific rotation $[\alpha]_D^{25} = +23°$ (c=1, methanol) and values of elemental analysis coincident with the theoretical values of $C_{33}H_{59}N_5O_{14}\cdot H_2O$ (C 51.62%, H 8.01%, N 9.12%). This substance gives a single spot positive to ninhydrin reaction at Rf 0.67 on the same thin layer chromatography as in (i) above.

(iv) 2',6'-Di-N-tert-butoxycarbonyl-3',4'-dideoxy-3',4'-didehydrokanamycin B of formula IX wherein $R_1$ and $R_4$ each represent hydrogen and $R_2$ and $R_3$ each represent tert-butoxycarbonyl group is in the form of a white powder with a decomposition point of 147°–148° C., a specific rotation $[\alpha]_D^{26} = +21°$ (c=1, methanol) and values of elemental analysis coincident with the theoretical values of $C_{28}H_{51}N_5O_{12}\cdot H_2O$ (C 50.36%, H 8.00%, N 10.49%). This substance gives a single spot positive to nynhydrin reaction at Rf 0.34 on the same thin layer chromatography as in (i) above.

(v) 6'-N-tert-Butoxycarbonyl-3',4'-dideoxy-3',4'-didehydrokanamycin B of formula IX wherein $R_1$, $R_2$ and $R_4$ each represent hydrogen and $R_3$ represents tert-butoxycarbonyl group is in the form of a white powder with a decomposition point of 145°–147° C., a specific rotation $[\alpha]_D^{26} = +27°$ (c=1, methanol) and values of elemental analysis coincident with the theoretical values of $C_{23}H_{43}N_5O_{10}\cdot H_2O$ (C 48.67%, H 7.99%, N 12.34%). This substance gives a single spot positive to nynhydrin reaction at Rf 0.19 on the same thin layer chromatography as in (i) above.

We have further found that 1-N-(L-4-benzyloxycarbonylamino-2-hydroxybutyryl)- and 1-N-(N-benzyloxycarbonylisoseryl)-3',4'-dideoxy-3',4'-didehydrokanamycin B, both of which are novel compounds prepared as intermediates in the process according to this invention by protecting all or some of the amino groups other than the 1-amino group of 3',4'-dideoxy-3',4'-didehydrokanamycin B with tert-butoxycarbonyl group, reacting an active ester of L-4-benzyloxycarbonylamino-2-hydroxybutyric acid or of N-benzyloxycarbonylisoserine with a mixture of the amino-protected derivatives so formed and treating the mixed N-acylated derivatives with trifluoroacetic acid to preferentially eliminate the tert-butoxycarbonyl groups, can be easily isolated and purified from other N-acylated by-products by column chromatography on macroreticular resins such as Diaion HP-20 (a commercial product of Mitsubishi Chemical Industries Limited). Thus, according to the process of this invention, it is possible to use different amino-protecting groups for the protection of the amino group or groups on the moiety of 3',4'-dideoxy-3',4'-didehydrokanamycin B and for the protection of the amino group on the moiety of L-4-amino-2-hydroxybutyric acid or of isoserine.

According to a further aspect of this invention, therefore, there are provided new compounds of the formula:

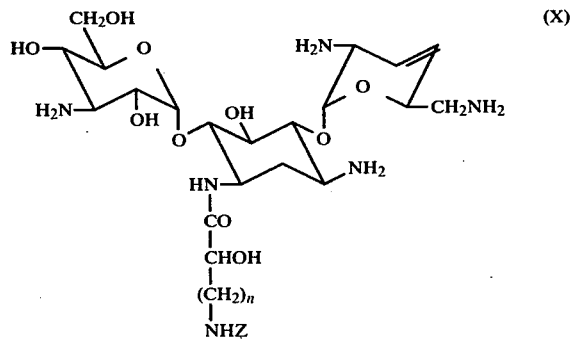

wherein n is 1 or 2 and Z represents benzyloxycarbonyl group, that is 1-N-(L-4-benzyloxycarbonylamino-2-hydroxybutyryl)- and 1-N-(N-benzyloxycarbonylisoseryl)-3',4'-dideoxy-3',4'-didehydrokanamycin B. In the latter compound, the isoseryl group may be D-, L- or DL-isoseryl group. Typical properties of the new compounds of formula X are given below.

(i) 1-N-(L-4-Benzyloxycarbonylamino-2-hydroxybutyryl)-3',4'-dideoxy-3',4'-didehydrokanamycin B is a white powder in the form of its monocarbonate monohydrate with a decomposition point of 120°–123° C., a specific rotation $[\alpha]_D^{27} = +26°$ (c=0.5, water) and values of elemental analysis coincident with the theoretical values of $C_{30}H_{48}N_6O_{12}\cdot H_2CO_3\cdot H_2O$ (C 48.68%, H 6.85%, N 10.99%). This substance gives a single spot at Rf 0.35 on a thin layer chromatography of silica gel with a solvent system of butanol-ethanol-chloroform-17% aqueous ammonia (4:5:2:3 by volume) as developer.

The compounds of formula X are advantageous over the known 1-N-(L-4-benzyloxycarbonylamino-2-hydroxybutyryl)-or 1-N-(N-benzyloxycarbonylisoseryl)-3',4'-dideoxykanamycin B prepared by reacting 3',4'-dideoxykanamycin B with an active ester of L-4-benzyloxycarbonylamino-2-hydroxybutyric acid or of N-benzyloxycarbonylisoserine in that they can be isolated and purified from other N-acylated by-products on column chromatography much more efficiently and thus in a higher purity than the latter (refer to Example 2 and Comparative Example 1 hereinafter given).

According to our further discovery, 1-N-(L-4-amino-2-hydroxybutyryl)- and 1-N-isoseryl-3',4'-dideoxy-3',4'-didehydrokanamycin B each of which is a novel compound prepared as an intermediate in the process according to this invention by the elimination of all the amino-protecting groups from the corresponding acylated product of formula VIII possess a high antimicrobial activity in themselves and find their applications also as antimicrobial agents.

Therefore, there are further provided, as another aspect of this invention, new compounds of the formula:

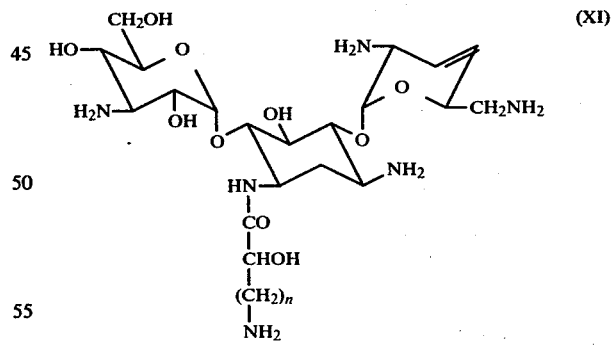

wherein n is 1 or 2, that is 1-N-(L-4-amino-2-hydroxybutyryl)- and 1-N-isoseryl-3',4'-dideoxy-3',4'-didehydrokanamycin B. In the latter compound, the isoseryl group may be in the D-, L- or DL-form. Typical properties of the new compounds of formula XI are given below. (i) 1-N-(L-4-amino-2-hydroxybutyryl)-3',4'-dideoxy-3',4'-didehydrokanamycin B is a white powder in the form of its dicarbonate with a decomposition point of 137°–142° C., a specific rotation $[\alpha]_D^{27} = +24°$ (c=0.5, water) and values of elemental analysis coincident with the theoretical values of $C_{22}H_{42}N_6O_{10}\cdot 2H-$ $_2CO_3$ (C 42.73%, H 6.87%, N 12.46%). This substance gives a single spot at Rf 0.34 on a thin layer chromatography of silica gel with a solvent system of butanol-ethanol-chloroform-28% aqueous ammonia (4:5:2:8 by volume) as developer. (ii) 1-N-(L-isoseryl)-3',4'-dideoxy-3',4'-didehydrokanamycin B is a white powder in the form of its 3/2 sulphate with a decomposition point of 190°–242° C. and a specific rotation $[\alpha]_D^{25} +21.9°$ (c=0.16, water). This substance gives a single spot at Rf 0.47 on a thin layer chromatography of silica gel with a solvent system of ethanol-butanol-chloroform-28% aqueous ammonia (3:5:2:7 by volume) as developer.

Antimicrobial spectra of 1-N-(L-isoseryl)- and 1-N-(L-4-amino-2-hydroxybutyryl)-3',4'-dideoxy-3',4'-didehydrokanamycin B (1-AHP-eno-DKB and 1-AHB-eno-DKB) are shown in the following table together with that of 1-N-(L-4-amino-2-hydroxybutyryl)-3',4'-dideoxykanamycin B (1-AHB-DKB).

The minimum inhibitory concentrations (mcg/ml) of the compounds tested against various microorganisms were determined according to a serial dilution method using nutrient agar medium at 37° C., the estimation being effected after 20 hours-incubation.

| | Antibacterial activity | | |
|---|---|---|---|
| | MIC (μg/ml) | | |
| Test organisms | 1-AHB-eno-DKB | 1-AHP-eno-DKB | 1-AHB-DKB |
| Sta. aureus Rosenbach FDA 209-P JC-1 | 0.10 | 0.10 | 0.05 |
| Sta. aureus Smith S-424 | 0.20 | 0.39 | 0.39 |
| Sta. aureus No. 26 | 0.78 | 0.39 | 0.78 |
| Sta. aureus ApO-1 | 0.39 | 0.78 | 0.20 |
| Sta. aureus N-0089 | 0.20 | 0.39 | 0.39 |
| Sta. epidermidis ATCC 14990 | 0.10 | 0.20 | 0.10 |
| Sta. epidermidis 109 | 0.20 | 0.20 | 0.20 |
| Str. faecalis ATCC 8043 | 50 | 50 | 50 |
| B. subtilis ATCC 6633 | 0.20 | 0.20 | 0.10 |
| B. anthracis No. 119 | 0.10 | 0.20 | 0.10 |
| E. coli (M) Cast. & Chalm.NIHJ JC-2 | 3.13 | 3.13 | 1.56 |
| E. coli No. 29 | 3.13 | 6.25 | 3.13 |
| E. coli W 677(A-20684) | 0.78 | 0.78 | 0.20 |
| E. coli JR 66/W 677(A-20683) | 3.13 | 3.13 | 1.56 |
| E. coli A-0001 | 3.13 | 6.25 | 3.13 |
| E. coli A-0003 | 3.13 | 6.25 | 3.13 |
| Sal. typhi 0-901-W | 0.78 | 1.56 | 0.39 |
| Sal. typhimurium LT-2 | 1.56 | 3.13 | 1.56 |
| Sal. enteritidis No. 11(Tōkai) | 1.56 | 3.13 | 1.56 |
| Sal. species D-0001 | 3.13 | 6.25 | 1.56 |
| Sal. species D-0006 | 1.56 | 6.25 | 1.56 |
| Sal. species D-0029 | 6.25 | 6.25 | 3.13 |
| Shigella dysenteriae Shigae | 0.78 | 1.56 | 0.78 |
| Kleb. pneumoniae | 1.56 | 1.56 | 0.78 |
| Kleb. pneumoniae 22# 3038 (A-20680) | 1.56 | 1.56 | 0.78 |
| Pro. morganii Kōno | 1.56 | 3.13 | 3.13 |
| Pro. vulgaris OX$_{19}$ | 3.13 | 3.13 | 3.13 |
| Pro. vulgaris J-0001 | 1.56 | 3.13 | 1.56 |
| Pro. rettgelli J-0026 | 6.25 | 25 | 6.25 |
| Pro. mirabilis J-0010 | 1.56 | 3.13 | 1.56 |
| Serra. marcescens No. 1 | 6.25 | 3.13 | 3.13 |
| Serra. marcescens No. 2 | 6.25 | 3.13 | 3.13 |
| Serra. marcescens I-0043 | 1.56 | 1.56 | 1.56 |
| Ps. aeruginosa IAM-1007 | 1.56 | 0.78 | 1.56 |
| Ps. aeruginosa NC-5 | 6.25 | 3.13 | 6.25 |
| Ps. aeruginosa E-2 | 3.13 | 3.13 | 6.25 |
| Ps. aeruginosa IID 1210 (IFO 3455) | 6.25 | 3.13 | 12.5 |
| Ps. aeruginosa M-0002 | 3.13 | 1.56 | 3.13 |
| Ps. aeruginosa M-0032 | 12.5 | 6.25 | 12.5 |
| Ps. aeruginosa M-0148 | 3.13 | 1.56 | 6.25 |

The following Examples further illustrate, but not limit, this invention.

EXAMPLE 1

3',4'-Dideoxy-3',4'-didehydrokanamycin B (449.5 mg, 1 mmol) is dissolved in a 50% aqueous isopropyl alcohol (22.4 ml) and triethylamine (0.56 ml, 4 mmol) and a solution of tert-butyl-S-4,6-dimethylpyrimid-2-ylthiocarbonate (14.41 g, 6 mmol) in isopropyl alcohol (11.2 ml) are added, in order, to the resulting solution. The solution is heated to 50° C. and held at this temperature for 22 hours under stirring to complete the desired amino-protecting reaction, i.e. the introduction of tert-butoxycarbonyl groups. To the resulting reaction solution containing 3,2',6',3''-tetra-N-tert-butoxycarbonyl, 3,2',6'-tri-N-tert-butoxycarbonyl, 2',6',3''-tri-N-tert-butoxycarbonyl, 2',6'-di-N-tert-butoxycarbonyl and 6'-N-tert-butoxycarbonyl derivatives of 3',4'-dideoxy-3',4'-didehydrokanamycin B thus formed, is added a solution of N-hydroxysuccinimide ester of L-4-benzyloxycarbonylamino-2-hydroxybutyric acid (525 mg, 1.5 mmol) in methyl alcohol (10 ml) and the mixture is stirred at room temperature for 4.5 hours to effect the 1-N-acylation intended. The reaction mixture is concentrated to dryness in vacuo and the residue is mixed with a 90% aqueous trifluoroacetic acid (10 ml) and allowed to stand at room temperature for 30 minutes to cause the elimination of tert-butoxycarbonyl groups. The reaction mixture is then diluted with water (4 ml) and passed through a column of 100 ml of a macroreticular resin commercially available as the trade name of Diaion HP-20AG. The column is then developed with water to collect the eluate in 10 ml-fractions and the fractions Nos. 9–13 are combined together and concentrated in dryness in vacuo, affording a powdery residue (1.006 g) containing unreacted 3',4'-dideoxy-3',4'-didehydrokanamycin B. The powder is dissolved in water (2 ml) and the solution is adjusted the pH to 7 with the addition of an aqueous ammonia and passed through a column of 20 ml of a weakly acidic cation exchange resin commercially available as the trade name of Amberlite CG-50 (NH$_4^+$ form). The column is then washed with water and eluted with 0.5 N aqueous ammonia, thus giving 3',4'-dideoxy-3',4'-didehydrokanamycin B (152 mg, recovery 34%).

The fractions Nos. 27–34 eluted from the Diaion column are collected together and concentrated to dryness in vacuo, yielding a powdery residue (262 mg) containing 1-N-(L-4-benzyloxycarbonylamino-2-hydroxybutyryl)-3',4'-dideoxy-3',4'-didehydrokanamycin B trifluoroacetate. The powder is dissolved in a 80% aqueous acetic acid (10 ml), to which platinum oxide is then added and the mixture is shaken under a pressure of 3.3 kg/cm$^2$ of hydrogen gas for 18 hours to effect the elimination of the benzyloxycarbonyl groups and the hydrogenation of the 3',4'-double bond simultaneously. The reaction solution is then concentrated in vacuo and the concentrate is diluted with water (10 ml), adjusted the pH to 7 with the addition of an aqueous ammonia and then passed through a column of 95 ml of Amberlite CG-50 (NH$_4^+$ form). The column is then washed with water and eluted with 0.8 N aqueous ammonia, yielding 1-N-(L-4-amino-2-hydroxybutyryl)-3',4'-dideoxykanamycin B (78 mg) in the form of a white powder. Yield 14.1%.

EXAMPLE 2

3',4'-Dideoxy-3',4'-didehydrokanamycin B (449.5 mg, 1 mmol) is dissolved in a 50% aqueous isopropyl alcohol (22.4 ml), and triethylamine (0.56 ml, 4 mmol) and a solution of tert-butyl-S-4,6-dimethylpyrimid-2-ylthiocarbonate (1.201 g, 5 mmol) in isopropyl alcohol (11.2 ml) are added, successively, to the resulting solution. The solution thus formed is heated to 50° C., held at this temperature for 16.5 hours under stirring, then adjusted the pH to 10 with the addition of an aqueous ammonia and stirred for further 20 minutes. Then, ethyl acetate (67 ml) is added to the reaction solution and the resulting mixture is shaken for 30 minutes, after which a phase separation occurs on standing and the ethyl acetate layer is separated and concentrated to dryness in vacuo, affording a mixture (944 mg) containing mainly tri-, tetra- and penta-N-tert-butoxycarbonyl derivatives of 3',4'-dideoxy-3',4'-didehydrokanamycin B in the form of a powder.

The mixture (944 mg) is dissolved in a 70% aqueous tetrahydrofuran (19 ml), to which is then added a solution of N-hydroxysuccinimide ester of L-4-benzyloxycarbonylamino-2-hydroxybutyric acid (525 mg, 1.5 mmol) in tetrahydrofuran (6 ml) and the mixture is stirred at room temperature for 20 hours to effect the 1-N-acylation and then concentrated to dryness in vacuo to give a powdery residue.

The powder (1.675 g) is dissolved in a 90% aqueous trifluoroacetic acid (8 ml) and the solution is allowed to stand at room temperature for 45 minutes to cause the elimination of the tert-butoxycarbonyl groups. The reaction solution is diluted with water (2 ml) and passed through a column of 100 ml of Diaion HP-20AG. The column is developed with water to collect the eluate in 10 ml-fractions. The fractions Nos. 7–4 are combined together and concentrated to dryness in vacuo, giving a powdery residue (559 mg) containing the unreacted 3',4'-dideoxy-3',4'-didehydrokanamycin B trifluoroacetate. The powder is dissolved in water (2 ml) and the solution is adjusted the pH to 7 with the addition of an aqueous ammonia and passed through a column of 20 ml of Amberlite CG-50 ($NH_4^+$ form). The column is washed with water and eluted with 0.5 N aqueous ammonia to recover 3',4'-dideoxy-3',4'-didehydrokanamycin B (97 mg, recovery 22%).

The fractions Nos. 25–37 eluted from the Diaion column are collected together and concentrated to dryness in vacuo, affording a powdery residue (270 mg) containing 1-N-(L-4-benzyloxycarbonylamino-2-hydroxybutyryl)-3',4'-dideoxy-3',4'-didehydrokanamycin B trifluoroacetate (purity: 39.3%). The powder is dissolved in a 95% aqueous acetic acid (15 ml), to which platinum oxide is then added and the mixture is shaken under a pressure of 3.4 kg/cm² of hydrogen to effect the elimination of the benzyloxycarbonyl groups and the hydrogenation of the 3',4'-double bond, simultaneously. The reaction solution is adjusted the pH to 7 with the addition of an aqueous ammonia and passed through a column of 100 ml of Amberlite CG-50 ($NH_4^+$ form). The column is washed with water and eluted with 0.75 N aqueous ammonia to yield 1-N-(L-4-amino-2-hydroxybutyryl)-3',4'-dideoxykanamycin B (89 mg) in the form of a white powder. Yield 16.1%.

EXAMPLE 3

3',4'-Dideoxy-3',4'-didehydrokanamycin B (1.8 g, 4 mmol) is dissolved in a 50% aqueous isopropyl alcohol (90 ml), and triethylamine (2.2 ml, 16 mmol) and tert-butyl-S-4,6-dimethylpyrimid-2-ylthiocarbonate (3.84 g, 16 mmol) are added, successively, to the resulting solution. The mixture is heated to 50° C. and held at this temperature for 23 hours under stirring and then concentrated to dryness in vacuo to give a yellow powder (5.17 g). The powder is dissolved in a mixture of chloroform (50 ml) and methanol (5 ml) and the solution is subjected to a chromatographic separation on a column of 500 g of a silica gel commercially available under the trade name of Wako Gel C-200 (a product of Wako Junyaku K. K., Japan). The column is washed with a solvent mixture of chloroform-methanol (10:1 by volume) and then eluted, in order, with a solvent mixture (15,440 ml) of chloroform-methanol-17% aqueous ammonia (100:10:1 by volume) to collect the eluate as the fractions Nos. 1–772, with a mixture (3,960 ml) of the same three solvents as above (80:10:1 by volume) for the fractions Nos. 773–970, with a mixture (7,100 ml) of the same three solvents (50:10:1 by volume) for the fractions Nos. 971–1325, with a mixture (13,600 ml) of the same three solvents (10:10:1 by volume) for the fractions Nos. 1326–2005 and with a mixture (4,400 ml) of the same three solvents (5:5:1 by volume) for the fractions Nos. 2006–2220.

The fractions Nos. 351–550 are combined together and concentrated to dryness in vacuo, yielding a mixture of tetra-N-tert-butoxycarbonyl derivatives (605 mg, 0.68 mmol, 17.1%). In the same manner as the above, the fractions Nos. 675–930 afford 2',6',3''-tri-N-tert-butoxycarbonyl derivative (196 mg, 0.26 mmol, 6.5%), the fractions Nos. 1091–1290 give 3,2',6'-tri-N-tert-butoxycarbonyl derivative (638 mg, 0.83 mmol, 20.8%), the fractions Nos. 1604–1990 yield 2',6'-di-N-tert-butoxycarbonyl derivative (679 mg, 1.02 mmol, 25.5%) and the fractions Nos. 2121–2220 yield 6'-N-tert-butoxycarbonyl derivative (189 mg, 0.33 mmol, 8.3%).

The mixture (605 mg) of tetra-N-tert-butoxycarbonyl derivatives obtained as above-mentioned is purified by a chromatographic separation using a column of 80 g of silica gel (Wako Gel C-200) with the elution using chloroform-methanol (7:1 by volume) to collect the eluate in 17 ml-fractions. The fractions Nos. 41–170 are combined together and concentrated to dryness in vacuo, giving 3,2',6',3''-tetra-N-tert-butoxycarbonyl derivative (196 mg, 0.22 mmol, 5.5%).

EXAMPLE 4

3,2',6',3''-Tetra-N-tert-butoxycarbonyl-3',4'-dideoxy-3',4'-didehydrokanamycin B (30 mg, 0.034 mmol) obtained in Example 3 is dissolved in dioxane (0.3 ml) and to the resulting solution is added a solution of N-hydroxysuccinimide ester of L-4-benzyloxycarbonylamino-2-hydroxybutyric acid (15 mg, 0.042 mmol) in dioxane (0.3 ml) and the mixture is stirred at room temperature for 17 hours. The reaction solution is concentrated to dryness in vacuo and the resulting white powder (49.4 mg) is dissolved in a 90% aqueous trifluoroacetic acid (1 ml), to which 5% palladium-carbon (20 mg) is then added, and the mixture is subjected to catalytic reduction in a stream of hydrogen at room temperature for 7 hours, whereby the elimination of the amino-protecting groups and the hydrogenation of the 3',4'-doublebond occur simultaneously. After the removal of the catalyst by filtration, the reaction solution is concentrated to dryness in vacuo and the residue is dissolved in water (0.5 ml). The solution is adjusted the pH to 7.4 with the addition of an aqueous ammonia and then passed through a column of 7 ml of Amberlite CG-50 (NH$_4^+$ form). The column is washed with water (30 ml), 0.3 N aqueous ammonia (30 ml) and 0.5 N aqueous ammonia (30 ml), successively, and then eluted with 0.7 N aqueous ammonia to yield the desired 1-N-(L-4-amino-2-hydroxybutyryl)-3',4'-dideoxykanamycin B (15.3 mg). Yield 82.4%.

EXAMPLE 5

3,2',6'-Tri-N-tert-butoxycarbonyl-3',4'-dideoxy-3',4'-didehydrokanamycin B (90 mg, 0.12 mmol) obtained in Example 3 is dissolved in a mixture (1.8 ml) of dioxane and water (1:1 by volume) and to the resulting solution N-hydroxysuccinimide ester of L-4-benzyloxycarbonylamino-2-hydroxybutyric acid (51 mg, 0.14 mmol) is added at room temperature under stirring and the mixture is held at that temperature under stirring for 17 hours.

The reaction solution is concentrated to dryness in vacuo and the residual white powder (149.9 mg) is dissolved in a 90% aqueous trifluoroacetic acid (1.5 ml). After the solution is allowed to stand at room temperature for 45 minutes, water (1.5 ml) is added thereto and the solution is passed through a column of 13 ml of Diaion HP-20AG (100-200 mesh in particle size). The column is eluted with water to collect fractions containing 1-N-(L-4-benzyloxycarbonylamino-2-hydroxybutyryl)-3',4'-dideoxy-3',4'-didehydrokanamycin B together. The combined eluate fractions are concentrated to dryness in vacuo and the residual white powder (28.5 mg) is dissolved in a mixture (1 ml) of acetic acid-methanol-water (1:1:1 by volume), to which 5% palladium-carbon (20 mg) is added and the mixture is subjected to catalytic reduction in a stream of hydrogen at room temperature for 5 hours. After the catalyst is removed by filtration, the reaction solution is concentrated to dryness in vacuo and the residue is dissolved in water (1 ml) and the resulting solution is adjusted the pH to 9.2 with the addition of an aqueous ammonia and then passed through a column of 7 ml of Amberlite CG-50 (NH$_4^+$ form). The column is washed with water (30 ml) and then 0.3 N aqueous ammonia (30 ml) and eluted with 0.75 N aqueous ammonia to yield 1-N-(L-4-amino-2-hydroxybutyryl)-3',4'-dideoxykanamycin B (23.0 mg). Yield 35.0%.

EXAMPLE 6

2',6',3''-Tri-N-tert-butoxycarbonyl-3',4'-dideoxy-3',4'-didehydrokanamycin B (90 mg, 0.12 mmol) obtained in Example 3 is treated in the same manner as that used in Example 5. There is obtained 1-N-(L-4-amino-2-hydroxybutyryl)-3',4'-dideoxykanamycin B (33.6 mg). Yield 50.0%.

EXAMPLE 7

2',6'-Di-N-tert-butoxycarbonyl-3',4'-dideoxy-3',4'-didehydrokanamycin B (180 mg, 0.27 mmol) obtained in Example 3 is dissolved in a mixture (3.6 ml) of dioxane-water (1:1 by volume) and to the resulting solution is added N-hydroxy-succinimide ester of L-4-benzyloxycarbonylamino-2-hydroxybutyric acid (117 mg, 0.33 mmol) at room temperature under stirring. The stirring is continued at that temperature for 17 hours, after which the reaction solution is concentrated to dryness in vacuo and the residual white powder (305 mg) is dissolved in a 90% aqueous trifluoroacetic acid (1.8 ml). The solution is allowed to stand at room temperature for 45 minutes, diluted with water (2 ml) and then passed through a column of 13 ml of Diaion HP-20AG (100-200 mesh in particle size). The column is eluted with water to collect fractions containing 1-N-(L-4-benzyloxycarbonylamino-2-hydroxybutyryl)-3',4'-dideoxy-3',4'-didehydrokanamycin B together and the fractions so combined are concentrated to dryness in vacuo. The residual white powder (92.1 mg) is dissolved in a mixture (2 ml) of acetic acid-methanol-water (1:1:1 by volume), to which 5% palladium-carbon (50 mg) is then added and the mixture is subjected to catalytic reduction in a stream of hydrogen at room temperature for 4 hours. After the removal of the catalyst by filtration, the reaction solution is concentrated to dryness in vacuo and the resulting white powder is dissolved in water (2 ml). The solution is adjusted the pH to 7.2 with the addition of an aqueous ammonia and then passed through a column of 7 ml of Amberlite CG-50 (NH$_4^+$ form). The column is washed with water (30 ml) and then with 0.3 N aqueous ammonia (30 ml) and eluted with 0.77 N aqueous ammonia to yield 1-N-(L-4-amino-2-hydroxybutyryl)-3',4'-dideoxykanamycin B (23.4 mg). Yield 15.5%.

EXAMPLE 8

6'-N-tert-Butoxycarbonyl-3',4'-dideoxy-3',4'-didehydrokanamycin B (100 mg, 0.18 mmol) obtained in Example 3 is dissolved in a mixture (2 ml) of dioxane-water (1:1 by volume) and to the resulting solution is added N-hydroxy-succinimide ester of L-4-benzyloxycarbonylamino-2-hydroxybutyric acid (77 mg, 0.22 mmol) at room temperature under stirring and the mixture is held at that temperature under stirring for 17 hours.

The reaction solution thus obtained is concentrated to dryness in vacuo and the residual white powder (179 mg) is dissolved in a 90% aqueous trifluoroacetic acid (1.8 ml). The solution is allowed to stand at room temperature for 45 minutes, diluted with water (2 ml) and passed through a column of 13 ml of Diaion HP-20AG (100-200 mesh in particle size). The column is eluted with water to collect the eluate fractions containing 1-N-(L-4-benzyloxycarbonylamino-2-hydroxybutyryl)-3',4'-dideoxy-3',4'-didehydrokanamycin B together and the fractions so combined are concentrated to dryness in vacuo. The resulting white powder (32.3 mg) is dissolved in a mixture (1 ml) of acetic acid-methanol-water (1:1:1 by volume), to which 5% palladium-carbon (30 mg) is added and the mixture is subjected to catalytic reduction in a stream of hydrogen at room temperature for 4 hours. After the catalyst is removed by filtration, the reaction solution is concentrated to dryness in vacuo and the residue is dissolved in water (1 ml). The solution is adjusted the pH to 7.8 with the addition of an aqueous ammonia and passed through a column of 7 ml of Amberlite CG-50 (NH$_4^+$ form). The column is washed with water (30 ml) and then with 0.3 N aqueous ammonia (30 ml) and eluted with 0.77 N aqueous ammonia to yield 1-N-(L-4-amino-2-hydroxybutyryl)-3',4'-dideoxykanamycin B (5.0 mg). Yield 5.0%.

EXAMPLE 9

3,2',6',3''-Tetra-N-tert-butoxycarbonyl-3',4'-dideoxy-3',4'-didehydrokanamycin B (21 mg, 0.024 mmol) obtained in Example 3 is dissolved in a mixture of dioxane (0.2 ml) and triethylamine (0.01 ml) and to the resulting solution is added a solution of N-hydroxysuccinimide ester of L-4-benzyloxycarbonylamino-2-hydroxybutyric acid (13 mg, 0.037 mmol) in dioxane (0.2 ml)

and the mixture is stirred at room temperature for 22 hours.

The reaction solution is concentrated to dryness in vacuo and the resulting white powder (43.9 mg) is dissolved in a 90% aqueous trifluoroacetic acid (1 ml). The solution is allowed to stand at room temperature for 45 minutes and then concentrated to dryness in vacuo and the residue is washed with ether (approximately 2 ml) and dried. The resulting white powder is dissolved in water (0.5 ml) and the solution is adjusted the pH to 8.0 with the addition of an aqueous ammonia and passed through a column of 9 ml of Amberlite CG-50 ($NH_4^+$ form). The column is washed with water (50 ml) and then with 0.1 N aqueous ammonia (40 ml) and eluted with 0.15 N aqueous ammonia to yield 1-N-(L-4-benzyloxycarbonylamino-2-hydroxybutyryl)-3',4'-dideoxy-3',4'-didehydrokanamycin B (11.3 mg in the form of a purified powder). Yield 63%.

The powder thus obtained is subjected to catalytic reduction followed by chromatographic separation on a column of Amberlite CG-50 in the same manner as that used in Example 8 to yield 1-N-(L-4-amino-2-hydroxybutyryl)-3',4'-dideoxykanamycin B (8 mg). Yield 87%.

EXAMPLE 10

3,2',6',3''-Tetra-N-tert-butoxycarbonyl-3',4'-dideoxy-3',4'-didehydrokanamycin B (28 mg, 0.032 mmol) obtained in Example 3 is dissolved in a mixture of dioxane (0.3 ml) and triethylamine (0.01 ml) and to the resulting solution is added a solution of N-hydroxysuccinimide ester of L-4-tert-butoxycarbonylamino-2-hydroxybutyric acid (16.6 mg, 0.052 mmol) in dioxane (0.3 ml) and the mixture is stirred at room temperature for 22 hours.

The reaction solution is concentrated to dryness in vacuo and the residual white powder (51.0 mg) is dissolved in a 90% trifluoroacetic acid (1 ml). The solution so formed is allowed to stand at room temperature for 45 minutes and then concentrated to dryness in vacuo and the residue is washed with ether (approximately 2 ml) and dried to give a white powder which is then dissolved in water (0.5 ml). The solution is adjusted the pH to 7.6 with the addition of an aqueous ammonia and passed through a column of 9 ml of Amberlite CG-50 ($NH_4^+$ form). The column is washed first with water (50 ml) and then with 0.3 N aqueous ammonia and eluted with 0.78 N aqueous ammonia to yield 1-N-(L-4-amino-2-hydroxybutyryl)-3',4'-dideoxy-3',4'-didehydrokanamycin B (15.7 mg in the form of a purified powder). Yield 72%.

The powder so obtained is subjected to catalytic reduction and then to chromatographic separation on a column of Amberlite CG-50 in the same manner as in Example 8, giving 1-N-(L-4-amino-2-hydroxybutyryl)-3',4'-dideoxykanamycin B (15 mg). Yield 95%.

EXAMPLE 11

3',4'-Dideoxy-3',4'-didehydrokanamycin B (450 mg, 1 mmol) is dissolved in a mixture of a 50% aqueous isopropyl alcohol (22.4 ml) and triethylamine (0.56 ml) and to the resulting solution is added a solution of benzyl-S-4,6-dimethylpyrimid-2-ylthiocarbonate (1.64 g, 6 mmol) in isopropyl alcohol (11.2 ml) and the mixture is stirred at 50° C. for 22 hours to introduce the amino-protecting benzyloxycarbonyl groups in the starting kanamycin B molecule.

Then, a solution of N-hydroxysuccinimide ester of L-4-benzyloxycarbonylamino-2-hydroxybutyric acid (525 mg, 1.5 mmol) in methyl alcohol (10 ml) is added to the reaction solution containing a mixture of N-benzyloxycarbonyl derivatives of 3',4'-dideoxy-3',4'-didehydrokanamycin B and the mixture is stirred at room temperature for 5 hours.

The resulting reaction solution containing a mixture of N-benzyloxycarbonyl derivatives of 1-N-(L-4-benzyloxycarbonylamino-2-hydroxybutyryl)-3',4'-dideoxy-3',4'-didehydrokanamycin B is concentrated to dryness in vacuo and the residue is dissolved in a mixture (10 ml) of methanolacetic acid-water (1:1:1 by volume). 5% Palladium-carbon (150 mg) is added to the solution obtained, and the mixture is subjected to catalytic reduction in a stream of hydrogen at room temperature for 5 hours, whereby there occur the elimination of the benzyloxycarbonyl groups and the hydrogenation of the 3',4'-double bond, simultaneously. After the removal of the catalyst, the reaction solution is concentrated to dryness and the residue is dissolved in water (5 ml). The solution is adjusted the pH to 8.0 with the addition of an aqueous ammonia and then passed through a column of 50 ml of Amberlite CG-50 ($NH_4^+$ form). The column is washed with water and then eluted with 0.7 N aqueous ammonia to yield 1-N-(L-4-amino-2-hydroxybutyryl)-3',4'-dideoxykanamycin B (60 mg) as white powder. Yield 11%.

EXAMPLE 12

3,2',6',3''-Tetra-N-tert-butoxycarbonyl-3',4'-dideoxy-3',4'-didehydrokanamycin B (30 mg, 0.034 mmol) is dissolved in dioxane (0.3 ml) and to the resulting solution is added a solution of N-hydroxysuccinimide ester of L-4-benzyloxycarbonylamino-2-hydroxybutyric acid (15 mg, 0.042 mmol) in dioxane (0.3 ml) and the mixture is stirred at room temperature for 17 hours.

The reaction solution is concentrated to dryness in vacuo and the powdery residue is dissolved in a mixture (2 ml) of methanol and acetic acid (1:1 by volume). 5% Palladium-carbon (20 mg) is added to the solution and the mixture is subjected to catalytic reduction in a stream of hydrogen at room temperature for 7 hours, whereby the reduction of the 3',4'-olefinic bond and the elimination of N-benzyloxycarbonyl group are achieved, concurrently. The reaction mixture is filtered to remove the catalyst and the solution is concentrated to dryness in vacuo. The residue is dissolved in a 90% aqueous trifluoroacetic acid (1 ml) and the solution is held at room temperature for 1 hour so as to eliminate the amino-protecting group from the molecule. The reaction solution is concentrated to dryness in vacuo and the residue is dissolved in water (0.5 ml). The solution is adjusted the pH to 8.0 with the addition of an aqueous ammonia and passed through a column of 7 ml of Amberlite CG-50 ($NH_4^+$ form). The column is washed with water (30 ml) and then with 0.3 N aqueous ammonia and eluted with 0.7 N aqueous ammonia to yield 1-N-(L-4-amino-2-hydroxybutyryl)-3',4'-dideoxykanamycin B (14 mg) as white powder. Yield 71%.

EXAMPLE 13

3',4'-Dideoxy-3',4'-didehydrokanamycin B (450 mg, 1 mmol) is dissolved in a mixture of a 50% aqueous isopropyl alcohol (22 ml) and triethylamine (0.41 ml) and to the resulting solution is added tert-butyl-S-4,6-dimethylpyrimid-2-ylthiocarbonate (960 mg, 4 mmol) and the mixture is stirred at 50° C. for 22 hours. Then, there is added to the reaction solution a solution of N-hydroxysuccinimide ester of N-benzyloxycarbonyl-DL-isoserine (410 mg, 1.2 mmol) in dioxane (7.5 ml) and the mixture is stirred at room temperature for 28 hours.

The reaction solution thus obtained which contains a mixture of tert-butoxycarbonyl derivatives of 1-N-(N-benzyloxycarbonyl-DL-isoseryl)-3',4'-dideoxy-3',4'-didehydrokanamycin B is concentrated to dryness in vacuo and the residue (1.95 g) is dissolved in a 90% aqueous trifluoroacetic acid (20 ml). The solution is allowed to stand at room temperature for 45 minutes to complete the elimination of the amino-protecting tert-butoxycarbonyl groups and again concentrated to dryness in vacuo. The residue is dissolved in water (2 ml) and the solution is passed through a column of 50 ml of Diaion HP-20. The column is eluted with water and the eluate is collected in 5 ml-fractions. The fractions Nos. 11–17 are combined together and concentrated to dryness in vacuo to give a powdery residue (166 mg). The powder is dissolved in a mixture (4 ml) of methanol-acetic acid-water (1:1:1 by volume) and 5% palladium-carbon (100 mg) is added to the solution. The mixture is subjected to catalytic reduction in a stream of hydrogen at room temperature for 3 hours.

After the removal of the catalyst, the reaction solution is concentrated to dryness in vacuo and the residue (160 mg) is dissolved in water (4 ml). The solution so formed is adjusted the pH to 7.2 with the addition of an aqueous ammonia and passed through a column of 75 ml of Amberlite CG-50 ($NH_4^+$ form). The column is washed with water (180 ml) and then with 0.2 N aqueous ammonia (180 ml) and eluted with 0.3 N–0.6 N aqueous ammonia solutions in the manner of gradient elution to yield 1-N-DL-isoseryl-3',4'-dideoxykanamycin B (80 mg) as white powder. Yield 15%.

EXAMPLE 14

3,2',6',3''-Tetra-N-tert-butoxycarbonyl-3',4'-dideoxy-3',4'-didehydrokanamycin B (30 mg, 0.034 mmol) is dissolved in dioxane (0.3 ml) and to the resulting solution is added a solution of N-hydroxysuccinimide ester of N-tert-butoxycarbonyl-DL-isoserine (13 mg, 0.043 mmol) in dioxane (0.3 ml) and the mixture is stirred at room temperature for 2 hours. The reaction solution is concentrated to dryness in vacuo and the residue is dissolved in a 90% aqueous trifluoroacetic acid (1 ml) and 5% palladium-carbon (20 mg) is added thereto and the mixture is subjected to catalytic reduction in a stream of hydrogen at room temperature for 7 hours whereby there occur the elimination of the amino-protecting groups and the reduction of the 3',4'-olefinic bond, in one step. After the removal of the catalyst, the reaction solution is concentrated to dryness in vacuo and the residue is dissolved in water (0.5 ml). The solution is adjusted the pH to 7.2 with the addition of an aqueous ammonia and passed through a column of 7 ml of Amberlite CG-50 ($NH_4^+$ form). The column is washed with water (30 ml) and eluted with 0.5 N aqueous ammonia to yield 1-N-DL-isoseryl-3',4'-dideoxykanamycin B (17 mg). Yield 88%.

EXAMPLE 15

3,2',6',3''-Tetra-N-tert-butoxycarbonyl-3',4'-dideoxy-3',4'-didehydrokanamycin B (69 mg, 0.081 mmol) is dissolved in a mixture of dioxane (0.8 ml) and triethylamine (0.02 ml) and to the resulting solution is added a solution of N-hydroxysuccinimide ester of L-3-tert-butoxycarbonylamino-2-hydroxypropionic acid (i.e. N-tert-butoxycarbonyl-L-isoserine) (44 mg, 0.147 mmol) in dioxane (0.8 ml) and the mixture is stirred at room temperature for 22 hours as in Example 10.

The reaction solution thus obtained is treated in the same manner as in Example 10, yielding 1-N-(L-isoseryl)-3',4'-dideoxy-3',4'-didehydrokanamycin B (25 mg in the form of a purified powder). Yield 60%.

The powder (15 mg) is dissolved in water (0.5 ml) and the solution is adjusted the pH to 6.1 with the addition of 10% sulfuric acid and concentrated to dryness, giving 1-N-(L-isoseryl)-3',4'-dideoxy-3',4'-didehydrokanamycin B.3/2 $H_2SO_4$ (19 mg). $[\alpha]_D^{25} +21.9°$ (c=0.16, water).

The powder of the free base (10 mg) is subjected to catalytic reduction followed by chromatographic separation on a column of Amberlite CG-50 in the same manner as in Example 8, affording 1-N-(L-isoseryl)-3',4'-dideoxykanamycin B (9 mg).

COMPARATIVE EXAMPLE 1

By way of comparison, this Example illustrates the preparation of 1-N-(L-4-amino-2-hydroxybutyryl)-3',4'-dideoxykanamycin B using the procedure same as that used in Example 2 but starting from 3',4'-dideoxykanamycin B. Thus, 3',4'-dideoxykanamycin B (450 mg, 1 mmol) is dissolved in a 50% aqueous isopropyl alcohol (22.4 ml) and to the resulting solution are added triethylamine (0.56 ml) first and then a solution of tert-butyl-S-4,6-dimethylpyrimid-2-ylthiocarbonate (1.201 g, 5 mmol) in isopropyl alcohol (11.2 ml). The mixture is heated to 50° C. and held at this temperature for 16.5 hours under stirring, then adjusted the pH to 10 with the addition of an aqueous ammonia and stirred for further 20 minutes. Ethyl acetate (67 ml) is added to the resulting reaction solution and the mixture is shaken for 30 minutes. Then, the ethyl acetate layer separated is taken and concentrated to dryness in vacuo to yield a mixture of N-tert-butoxycarbonyl derivatives of 3',4'-dideoxykanamycin B (1.15 g) in the form of a powder.

The powder is dissolved in a 50% aqueous tetrahydrofuran (40 ml) and to the resulting solution is added a solution of N-hydroxysuccinimide ester of L-4-benzyloxycarbonylamino-2-hydroxybutyric acid (641 mg, 1.8 mmol) in tetrahydrofuran (10 ml) and the mixture is stirred at room temperature for 4 hours. The reaction solution so formed which contains a mixture of tert-butoxycarbonyl derivatives of 1-N-(L-4-benzyloxycarbonylamino-2-hydroxybutyryl)-3',4'-dideoxykanamycin B is concentrated to dryness in vacuo and the resulting powder (2.19 g) is dissolved in a 90% aqueous trifluoroacetic acid (5 ml). The solution is allowed to stand at room temperature for 1 hour to complete the elimination of the tert-butoxycarbonyl groups, diluted with water (10 ml) and passed through a column of 100 ml of Diaion HP-20AG. The column is eluted with water and the eluate is collected in 10 ml-fractions. The fractions Nos. 6–12 are combined together and concentrated to dryness in vacuo to leave a residual powder (540 mg) containing the unreacted 3',4'-dideoxykanamycin B trifluoroacetate. The powder is dissolved in water (5 ml) and the solution is passed through a column of 15 ml of Amberlite CG-50 ($NH_4^+$ form). The column is washed with water and eluted with 0.5 N aqueous ammonia to recover 3',4'-dideoxykanamycin B (141 mg). Recovery 31%.

The fractions Nos. 23–36 eluted from the Diaion column are combined together and concentrated to dryness in vacuo to leave a powder (258 mg) containing 1-N-(L-4-benzyloxycarbonylamino-2-hydroxybutyryl)-

3',4'-dideoxykanamycin B trifluoroacetate (purity 24.8%). The powder is dissolved in a mixture (3 ml) of methanol-acetic acid-water (1:1:1 by volume) and 5% palladium-carbon (50 mg) is added to the solution. The mixture is subjected to catalytic reduction in a stream of hydrogen at room temperature for 5 hours to eliminate the benzyloxycarbonyl groups. After the removal of the catalyst, the reaction solution is concentrated to dryness in vacuo, and the residue is dissolved in water (1.5 ml). The solution is adjusted the pH to 8.6 with the addition of an aqueous ammonia and passed through a column of 10 ml of Amberlite CG-50 ($NH_4^+$ form). The column is washed with water and eluted with 0.8 N aqueous ammonia to yield 1-N-(L-4-amino-2-hydroxybutyryl)-3',4'-dideoxykanamycin B (54 mg) as white powder. Yield 10%.

What we claim is:

1. A process for the preparation of 1-N-isoseryl- or 1-N-(L-4-amino-2-hydroxybutyryl)-3',4'-dideoxykanamycin B of the formula:

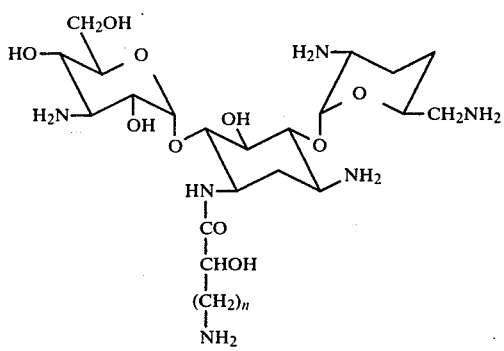

(I)

where n is 1 or 2 which comprises the steps of (1) providing 3',4'-dideoxy-3',4'-didehydrokanamycin B of the formula:

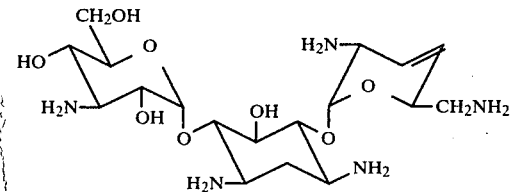

(II)

as starting compound;

(2) protecting all or some of the four amino groups other than the 1-amino group of the starting compound with an amino-protecting group;

(3) reacting the partially amino-protected derivative or derivatives thus obtained with isoserine or L-4-amino-2-hydroxybutyric acid or a reactive derivative thereof having the amino group unprotected or protected with an amino-protecting group to acylate the 1-amino group of the former;

(4) eliminating the amino-protecting group or groups of the acylated product; and (5) reducing the 3',4'-olefinic double bond of the product by a catalytic hydrogenation; the steps (4) and (5) being effected in order or simultaneously or in the reverse order.

2. A process according to claim 1 wherein the partially amino-protected derivative is 3,2',6',3''-tetra-N-protected derivative of 3',4'-dideoxy-3',4'-didehydrokanamycin B of the formula:

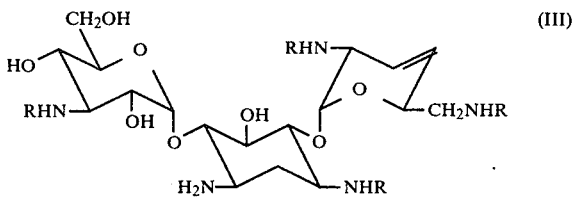

(III)

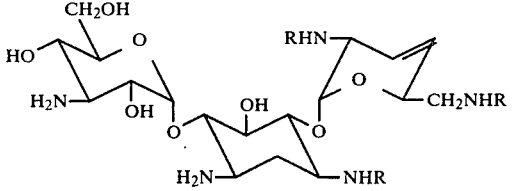

(IV)

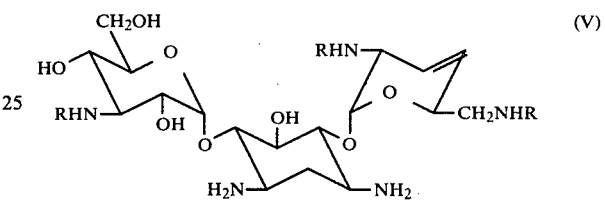

(V)

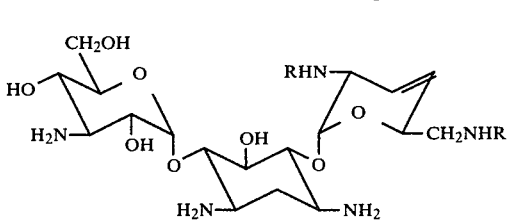

(VI)

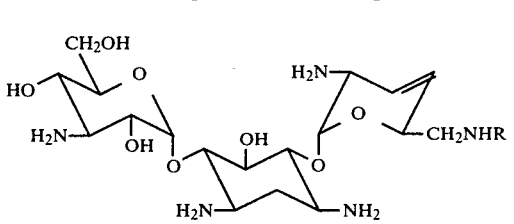

(VII)

where R represents an amino-protecting group.

3. A process according to claim 1 wherein the partially amino-protected derivative is 3,2',6'-tri-N-protected derivative of 3',4'-dideoxy-3',4'-didehydrokanamycin B of the formula:

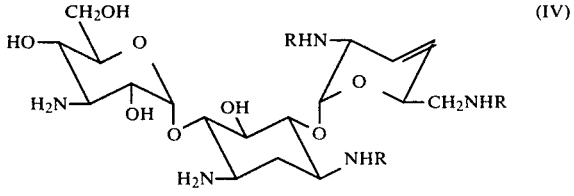

(IV)

where R represents an amino-protecting group.

4. A process according to claim 1 wherein the partially amino-protected derivative is 2',6',3''-tri-N-protected derivative of 3',4'-dideoxy-3',4'-didehydrokanamycin B of the formula:

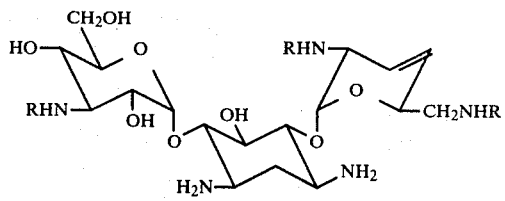

where R represents an amino-protecting group.

5. A process according to claim 1 wherein the partially amino-protected derivative is 2',6'-di-N-protected derivative of 3',4'-dideoxy-3',4'-didehydrokanamycin B of the formula:

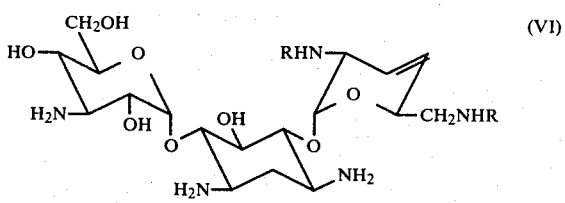

where R represents an amino-protecting group.

6. A process according to claim 1 wherein the partially amino-protected derivative is 6'-amino-N-protected derivative of 3',4'-dideoxy-3',4'-didehydrokanamycin B of the formula:

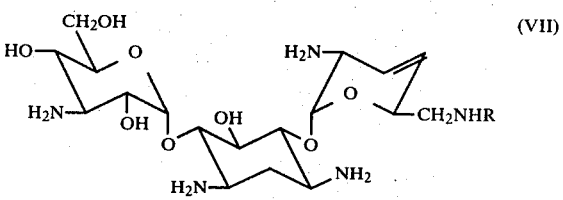

where R represents an amino-protecting group.

7. A process according to claim 1 wherein the partially amino-protected derivatives are a mixture of any two or more of the different amino-protected derivatives obtained by protecting all or some of the four amino groups other than the 1-amino group of 3',4'-dideoxy-3',4'-didehydrokanamycin B with an amino-protecting group.

8. A process for the preparation of 1-N-isoseryl- or 1-N-(L-4-amino-2-hydroxybutyryl)-3',4'-dideoxykanamycin B which comprises (1) protecting all or some of the four amino groups other than the 1-amino group of 3',4'-dideoxy-3',4'-didehydrokanamycin B with tert-butoxycarbonyl group, (2) reacting the tert-butoxycarbonyl derivative or derivatives of the starting compound thus formed with N-tert-butoxycarbonylisoserine or L-4-tert-butoxycarbonylamino-2-hydroxybutyric acid or a reactive derivative thereof to acylate the 1-amino group of the former, (3) eliminating all the tert-butoxycarbonyl groups of the acylated product and (4) reducing the 3',4'-olefinic double bond of the product by a catalytic hydrogenation, the steps (3) and (4) being effected in order or simultaneously or in the reverse order.

9. A process for the preparation of 1-N-isoseryl- or 1-N-(L-4-amino-2-hydroxybutyryl)-3',4'-dideoxykanamycin B which comprises (1) protecting all or some of the four amino groups other than the 1-amino group of 3',4'-dideoxy-3',4'-didehydrokanamycin B with tert-butoxycarbonyl group, (2) reacting the butoxycarbonyl derivative or derivatives of the starting compound thus formed with N-benzyloxycarbonylisoserine or L-4-benzyloxycarbonylamino-2-hydroxybutyric acid or a reactive derivative thereof to acylate the 1-amino group of the former, (3) eliminating the tert-butoxycarbonyl group or groups of the acylated product and (4) reducing the 3',4'-olefinic double bond and simultaneously eliminating the benzyloxycarbonyl group by a catalytic hydrogenation, the steps (3) and (4) being effected in order or simultaneously or in the reverse order.

10. An amino-protected derivative of 3',4'-dideoxy-3',4'-didehydrokanamycin B selected from the group consisting of 3,2',6',3''-tetra-N-tert-butoxycarbonyl-3',4'-dideoxy-3',4'-didehydrokanamycin B, 3,2',6'-tri-N-tert-butoxycarbonyl-3',4'-dideoxy-3',4'-didehydrokanamycin B, 2',6',3''-tri-N-tert-butoxycarbonyl-3',4'-dideoxy-3',4'-didehydrokanamycin B, 2',6'-di-N-tert-butoxycarbonyl-3',4'-dideoxy-3',4'-didehydrokanamycin B and 6'-N-tert-butoxycarbonyl-3',4'-dideoxy-3',4'-didehydrokanamycin B.

11. 1-N-(N-benzyloxycarbonylisoseryl)- or 1-N-(L-4-benzyloxycarbonylamino-2-hydroxybutyryl)-3',4'-dideoxy-3',4'-didehydrokanamycin B of the formula:

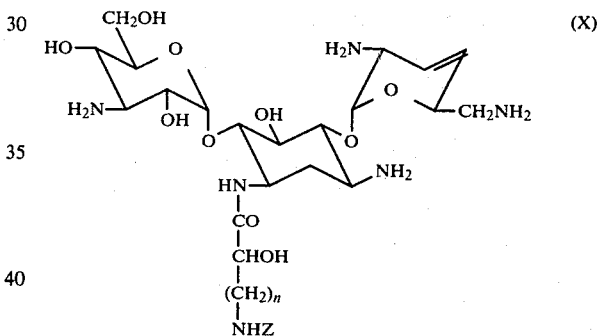

where Z represents benzyloxycarbonyl group and n is 1 or 2.

12. 1-N-isoseryl- or 1-N-(L-4-amino-2-hydroxybutyryl)-3',4'-dideoxy-3',4'-didehydrokanamycin B of the formula:

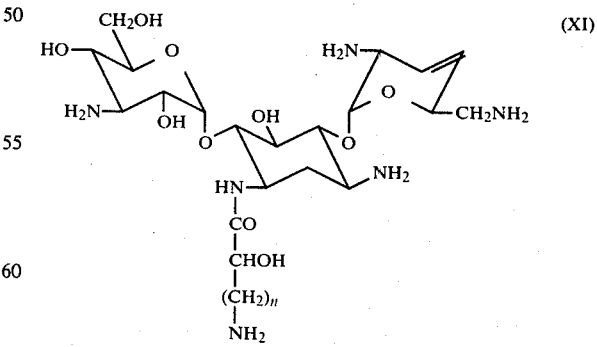

where n is 1 or 2.

* * * * *